United States Patent
Mirsky et al.

(10) Patent No.: US 6,458,600 B1
(45) Date of Patent: Oct. 1, 2002

(54) METHOD FOR PRODUCING LATERALLY ORGANIZED STRUCTURES ON SUPPORTING SURFACES

(75) Inventors: Vladimir M. Mirsky, Regensburg; Michael Riepl, Mallersdorf, both of (DE)

(73) Assignee: Otto Samuel Wolfbeis, Regensburg (DE)

(*) Notice: Subject to any disclaimer, the term of this patent is extended or adjusted under 35 U.S.C. 154(b) by 0 days.

(21) Appl. No.: 09/554,896

(22) PCT Filed: Nov. 20, 1998

(86) PCT No.: PCT/DE98/03437

§ 371 (c)(1),
(2), (4) Date: Nov. 20, 2000

(87) PCT Pub. No.: WO99/27355

PCT Pub. Date: Jun. 3, 1999

(30) Foreign Application Priority Data

Nov. 21, 1997 (DE) .......................... 197 51 658

(51) Int. Cl.[7] .............. G01N 33/543; G01N 33/53; G01N 21/00; G01N 33/00; G01N 27/26
(52) U.S. Cl. .............. 436/518; 436/512; 436/513; 436/536; 435/6; 435/7.1; 435/7.2; 422/50; 422/55; 422/57; 422/63; 422/68.1; 422/82.01; 422/82.02; 204/194; 204/280; 204/286; 204/400; 204/403; 204/406; 205/545; 205/640
(58) Field of Search .................. 422/50, 55, 57, 422/63, 68.1, 82.01, 82.02; 435/7.1, 6, 7.2; 436/512, 513, 518, 536; 204/194, 400, 403, 406, 280, 286; 205/640, 545

(56) References Cited

U.S. PATENT DOCUMENTS

| | | | | |
|---|---|---|---|---|
| 4,849,176 A | * | 7/1989 | Sakagami | 422/64 |
| 5,166,063 A | * | 11/1992 | Johnson | 435/173 |
| 5,436,161 A | * | 7/1995 | Bergstrom et al. | 435/291 |
| 5,443,701 A | * | 8/1995 | Willner et al. | 204/153.12 |
| 5,494,831 A | * | 2/1996 | Kindler | 204/193 |
| 5,653,939 A | * | 8/1997 | Hollis et al. | 204/456 |
| 5,965,452 A | * | 10/1999 | Kovacs | 436/149 |
| 6,387,625 B1 | * | 5/2002 | Eckhardt et al. | 324/715 |

FOREIGN PATENT DOCUMENTS

| | | | | |
|---|---|---|---|---|
| EP | 0402917 A2 | * | 6/1992 | 33/48 |
| WO | WO 96/28538 A1 | * | 9/1996 | |

* cited by examiner

*Primary Examiner*—Long V. Le
*Assistant Examiner*—Kartic Padmanabhan
(74) *Attorney, Agent, or Firm*—Martin Fleit; Paul D. Bianco; Fleit Kain Gibbons Gutman & Bongini (57) ABSTRACT

The present invention relates generally to a structure, on the surface of the support material of which structure molecular layers are immobilized so as to be electrically addressable, a method for the electrically addressable immobilization of molecules, a device for carrying out this method, and the use of this structure as a chemo- and/or biosensor, in particular as a multisensor system for chemical, biological, and physical assays, and for applications in the combinatorial synthesis on the boundary surface.

18 Claims, 5 Drawing Sheets

METHOD FOR PRODUCING LATERALLY ORGANIZED STRUCTURES ON SUPPORTING SURFACES

This is the National Stage Filing of PCT/DE98/03437 filed Nov. 20, 1998 and published Jun. 3, 1999.

BACKGROUND OF THE INVENTION

1. Field of the Invention

The present invention relates generally to a structure, on the surface of the support material of which structure molecular layers are immobilized so as to be electrically addressable, a method for the electrically addressable immobilization of molecules, a device for carrying out this method, and the use of this structure as a chemo- and/or biosensor, in particular as a multisensor system for chemical, biological, and physical assays, and for applications in the combinatorial synthesis on the boundary surface.

2. Prior Art

Both chemosensors and biosensors, i.e., comparatively small measuring arrangements, are increasingly needed to make it possible to carry out chemical or biochemical analyses rapidly and at the site of the occurrence. Compared to the immunological assay systems, they have the special advantage that they are able to quantify, preferably continuously, for example, concentrations of (bio)chemical substances within a short period of time and without a time-consuming preparation of the samples. A biosensor should therefore be small, which offers the additional advantage that it can be used in the vicinity of the site of the analysis; for example, using enzymatic biosensors, diabetics are able to determine their blood sugar level within a few minutes.

Thus, chemo- and biosensory analysis includes both detection and quantification. The process of molecular detection, for example, plays an important role in biology. For example, a cell should be able to detect a potassium ion and should not mistake it for a sodium ion which is very similar [to the potassium ion], the enzyme glucose dehydrogenase should only degrade glucose but not fructose, and the immune system should be able to recognize foreign organisms and substances that have invaded the system before it attacks them. This means that molecules that recognize the targeted substances are needed to make it possible to develop chemo- and biosensors. At the same time, the many other substances that exist side by side with the targeted ones must be ignored. Thus, a biosensor must be able to meet the following requirement, i.e., that the process of recognizing/coupling can be detected and "translated" into a measurable signal. During this "translation," however, serious problems arise so that there is a need for a system that makes detection easy. In systems that are used in the form of monosystems, it is not necessary to immobilize the molecules since only one single species has to be recognized and identified. If, on the other hand, multiple systems are to be used, such as multisensor systems, with which different molecules are to be detected at the same time, it is necessary to ensure an addressable immobilization of the molecular layers on the surface of the support material, thereby making it possible to detect the recognition of a signal. This type of system is not known in prior art.

In prior art, several methods for an addressable immobilization are available, with which it is possible to specifically couple several different types of molecules to a surface of the support material. Yershov et al. (Yershov, G., Barksy, V., Belgovskiy, A., Kirillov, E., Kreindlin, E., Ivanov, I., Parinov, S., Guschin, D., Drobishev, A., Dubiley, S., Mirzabekov, A., Proc. Natl. Acad. Sci. 43 (1996), pp. 4913–4916) as well as Blanchard et al. (Blanchard, A. P., Kaiser, R. J., Hood, L. E., Biosens. & Bioelectron. 11 (1996), pp. 687–690) describe the use of this technique, for example, to produce DNA arrays. In addition, these techniques are used for the micromechanical addressability and for the optical addressability. U.S. Pat. No. 5,412,087 describes the optical immobilization by coupling functional groups to photosensitive protecting groups. The system is activated by cleaving off the protecting groups by means of photolytic degradation. Chrisey et al. (Chrisey, L. A., O'Ferall, E., Spargo, B. J., Dulcey, C. S., Calvert, J. M., Nucl. Acids Res. 24 (1996), pp. 3040–3047) describe a different approach according to which the adsorption is carried out using the photoresist technique.

The known immobilization methods mentioned above, however, have many drawbacks which limit their applicability. Thus, for example, the resolution of the micromechanical immobilization is limited by the size of the individual spray particles. In the above-described method used by Yershov et al. (1996) and Blanchard et al. (1996), at best an optical resolution of approximately 100 $\mu$m is possible. During the optical immobilization according to U.S. Pat. No. 5,412,087, it is always necessary to work with protecting groups which require that specific conditions (such as solvents, darkening the work area because the protecting groups are sensitive to light, etc.) be maintained and which must be removed at a certain point in time. The above-mentioned photoresist technique by Chrisey et al. (1996) is very time- and cost-consuming since a large number of photomasks must be used.

SUMMARY OF THE INVENTION

Thus, the problem to be solved by the present invention is to make available a structure which is able to both bind and detect molecules and thus to make them qualitatively and quantitatively determinable. An additional problem to be solved by the present invention is to make available a method that makes it possible for molecules to be electrically addressably immobilized or desorbed on surfaces and thus to avoid the drawbacks mentioned. In addition, yet another problem to be solved by the present invention is to design a device for carrying out the method described by this invention and thus for manufacturing the structure described by this invention.

This problem is solved by making available a structure with electrically addressable immobilized molecules, which structure comprises a support material, one and/or a plurality (1 to n) of electrically conductive support surface(s) which is/are located on this support material, and one and/or a plurality of immobilized identical and/or different receptor (s).

Although it is known that it is possible to influence the chemical adsorption of molecules on an electrode by changing the applied chemical potential and that this dependence on the potential also applies to the chemical adsorption of thiol compounds on electrodes, the work that led to the present invention focused on the conditions under which, for example, the coupling between gold and sulfur is stable. Surprisingly, however, it was discovered that a chemically adsorbed molecular layer on an electrode is stable only within a specific pH-dependent range of potential. These results go far beyond the findings that have been described in the pertinent literature by Imabyashi et al. (Imabyashi, S., Iida, M., Hobara, D., Feng, Z. Q., Niki, K., Kakiushi, T., J. Electroanal. Chem. 428 (1997), pp. 33–38).

The problem of making available a method for the manufacture of a structure of the type mentioned above is solved by addressably immobilizing molecules on surfaces in a simply manner. This method comprises the following steps:

(a) a support material with n electrodes, where n stands for an integral number, is introduced into a flow-type cell which contains the electrolyte solution and the molecules to be immobilized (receptors), (b) either an adsorption potential or a desorption potential is applied to each separate electrode, as a result of which the uncoated electrode regions are kept inert by the desorption potential, and the adsorption potential that has already been applied to the coated electrode regions prevents the desorption of molecules as well as the adsorption of molecules that have a different structure, which ensures that the electrode region is occupied by the first type of molecules and the molecules are immobilized and securely coupled to the surface of the support material, and (c) the adsorption of molecules on the electrode(s) is measured as a change in the signal.

The process is concluded when a constant signal value is reached, e.g., a capacitance, impedance, or resonant frequency value.

The method described by this invention has the advantage that it makes it possible to control the desorption or adsorption of molecules by means of changing the potential within as well as outside the potential stability range. Based on this principle, it is possible to form a specific lateral structure of the chemically adsorbed layer.

Figure 1:
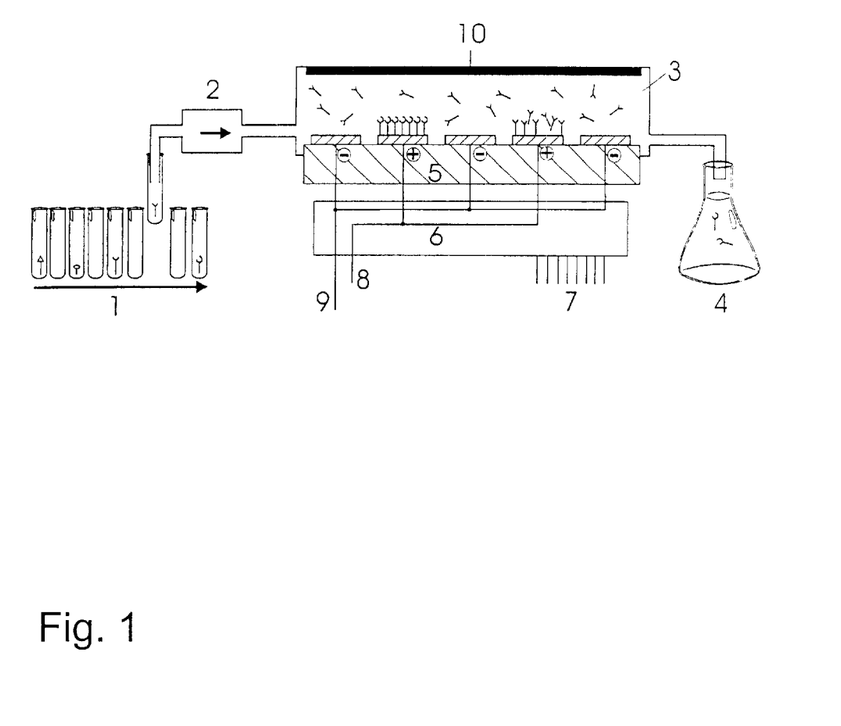
FIG. 1 presents a diagrammatic representation of the device for carrying out the electrically addressable immobilization procedure.

This method can be carried out using the device according to this invention which comprises an exchangeable device (1) for sample holders, a pump (2), a flow-type cell (3) into which the molecule or molecules desired or the receptor or receptors is/are transported by means of the pump (2), a support material (5) to which n electrodes are attached, with the support material (5) with n electrodes being located in the flow-type cell (3), a multiplexer (6), an address bus (7) which controls the multiplexer (6), as a result of which either an adsorption potential (8) or a desorption potential (9) is separately applied to the electrode(s) with respect to the reference electrode (10), and a collecting vessel (4) into which the excess molecules are pumped by means of the pump (2) once the molecules have been immobilized.

The structure according to this invention is used as a chemo- and/or biosensor, in particular as a multisensor system.

As such, the structure is preferably used directly in the sample medium, thus making an easy assay and/or detection possible by simply measuring the change in the signal value, in particular the capacitance, impedance, or resonant frequency value. In this manner, a system is made available by means of which the problems and disadvantages of the prior art systems mentioned above are avoided.

The structures according to this invention with the electrically addressable immobilized molecules can also be used for the combinatorial synthesis by specifically releasing molecules—which are coupled to the surface of the electrode and which, depending on the electrode, can be identical to or different from each other—by applying the desorption potential and thus by letting these molecules function as reaction participants during the synthesis step carried out or, if the synthesis is carried out on the surface, making it possible for the product to be cleaved off directly.

Figure 2:
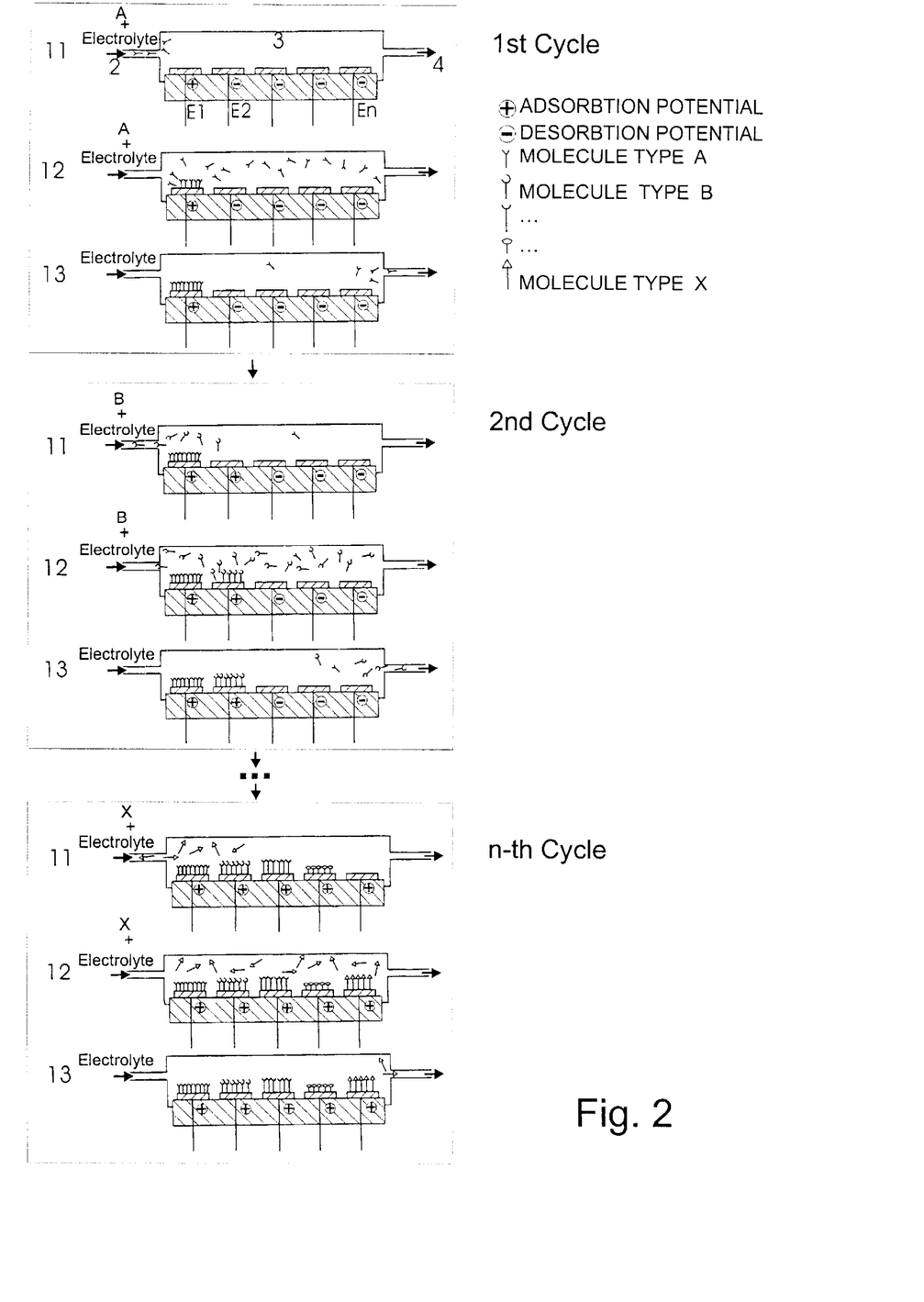
FIG. 2 shows how a chemo- and/or biosensor, especially a multisensor system ("array") with n separate electrodes (where n is an integral number), is subjected to an electrically addressable immobilization.

For the electrically addressable immobilization, any number of electrodes of random size and shape, which have been applied to a support material made of a dielectric material, can be used, and optionally, electrical leads for sensor spots can be incorporated into this dielectric material. The immobilization is carried out as shown in the diagrams of FIGS. 1 and 2 which will be described in greater detail below. During immobilization, different receptors (molecules A, B, C, etc.) which contain one or more thiol groups are specifically coupled to different electrodes (1, 2, 3, etc): receptor A to electrode E1, receptor B to electrode E2, etc. To obtain these couplings, the following steps are required: In a liquid electrolyte solution, a suitable electrode potential (adsorption potential) is applied to electrode E1 with respect to a reference electrode which supports the coupling to thiol groups. At the same time, an electrode potential (desorption potential) is applied to the other electrodes (2, 3, etc.) with respect to the same reference electrode which is able to suppress the coupling of the thiol groups to these electrodes. As a result, the added receptor molecule A is attached to electrode E1 only. Subsequently, the liquid electrolyte with the receptor molecules A is replaced with a liquid electrolyte solution with receptor molecules B, and these molecules are addressed to the next electrode site 2. By applying the desorption potential, the uncoated electrode sites are kept inert. The adsorption potential that is applied to the already coated electrode sites prevents the desorption of the molecules as well as the adsorption of differently structured molecules, since the electrode site is completely occupied by the first type of molecules. This process is repeated until the structure of the sensor has been completely built up. Between the immobilized molecule and the electrode, a permanent coupling is established. Thus, it is possible to produce a biosensor or a multisensor system ("array") with any molecular structure desired.

An additional benefit of the method described by the present invention pertains to the fact that, following the electrically addressable immobilization, it is possible for one or a plurality of molecular layer(s), e.g., antibodies or DNA strands, to be adsorbed and/or immobilized by way of functional groups to a random number (0 to n) of electrodes on which the receptors are located. For this purpose, the adsorption potential is maintained for all coated electrodes, and the liquid electrolyte solution of the molecules that are to be attached, in combination with a coupling reagent, are pumped simultaneously into the flow-type cell. As an alternative, it is also possible to first add the coupling reagent and then to add the molecules that are to be attached only once the activation of the base layer(s) has been concluded. If the molecules are able to attach themselves to the addressed layer on their own, there is no need for the coupling reagent, such as is the case with the avidin-biotin system, Ni-His tag, or hydrophobic-hydrophobic interactions of liposomes with unfunctionalized alkanethiol chains. After the molecules have been chemically or physically attached to the base layer(s), a liquid electrolyte solution is used to rinse and thus to remove unused or deactivated coupling reagent and/or uncoupled molecules from the cell. Depending on what field of application the detector system is to be used in, this process can be repeated several times until the desired structure of the sensor has been obtained.

Similarly, it is possible to coat two or more electrodes of the multisensor system ("array") by means of the adsorption potential and optionally modify them by means of a subsequent physical or chemical adsorption or coupling to one or several identical or different layers of molecules. Thus, if the desorption potential is applied to specific electrodes, these electrodes can be coated as described above with a different coating after the molecules have been desorbed and the desorbed molecules have been rinsed off. This process can be repeated until the multisensor structure desired has been obtained.

Suitable coupling reagents include, in particular, carbodiimides and derivatives thereof and N-succinimides and derivatives thereof.

Using the systems described above, it is possible to perform a screening procedure while carrying out different tests at the same time, thus making it possible to avoid having to carry out the separate and time-consuming screening procedures thus far required.

Suitable support materials include any solid dielectric substrate, in particular silicon, glass, any nonconductive synthetic material, such as Teflon, PVC, or PE, and any conductive or semiconductive substrate which is insulated from the electrode(s) by means of a dielectric layer.

The electrodes used are thin conductive materials which are intimately attached to the support material. In particular, suitable materials include Au, Pd, Pt, Ag, alloys, such as Au/Pd, Au/Ag, Ag/Pd, GaAs, and similar materials, doped semiconductors, and any other conductive or semiconductive inorganic or organic material, such as TCNQ, or TTF.

The reference electrodes used are electrodes generally used in electrochemistry, such as Ag/AgCl, etc., with and without a salt bridge.

The receptors, which are coupled to the electrodes by means of the process for the electrically addressable immobilization according to this invention, are molecules, the coupling of which to the electrodes can be controlled by the electrode potential. In most cases, these molecules contain a minimum of one thiol group or are coupled to a minimum of one thiol group or contain a sulfide or disulfide group. These molecules are selected from the group that comprises HS—$(CN_2)_n$—X, where n stands for a number from 2 to 24 and X stands for H, OH, SH, $CH_3$, COOH, $NH_2$, and any other molecular fragment, —X—$(CH_2)_n$—S—S—$(CH_2)_m$—Y or X—$(CH_2)_n$—S—$(CH_2)_m$—Y, where m and n stand for a number from 2 to 24 and X and Y stand for H, OH, SH, $CH_3$, COOH, $NH_2$ and any other molecular fragment, especially ω-mercapto acids, n-alkanethiols, such as octanethiol, as well as toxins, hormones, hormone receptors, peptides, proteins, enzymes, enzyme substrates, cofactors, drugs, lectins, sugars, oligonucleotides, DNA, RNA, viruses, bacteriophages, prions, oligosaccharides, natural and artificial receptors, redox-active substances, dyes, acids, bases, epitopes, antigens or antibodies which contain a minimum of one thiol group or which are coupled to a minimum of one thiol-containing compound. Similarly, these receptors may contain sulfide or disulfide groups. The thiol groups may be present in such molecules from the very beginning or they may have been introduced later by chemical modification. In addition, in all of the compounds mentioned above, an Se atom may be substituted for the S atom of the thiol group.

The molecules that may be additionally attached to the receptors are selected from the group that comprises toxins, hormones, hormone receptors, peptides, proteins, enzymes, enzyme substrates, cofactors, drugs, lectins, sugars, oligonucleotides, DNA, RNA, viruses, bacteriophages, prions, oligosaccharides, natural and artificial receptors, redox-active substances, dyes, acids, bases, epitopes, antigens or antibodies which contain a minimum of one functional group or which are able to enter into interactions with the adsorbed receptor, which makes it possible for them to be chemically and/or physically adsorbed and/or immobilized on the electrode(s).

As defined here, the adsorption potential is an electrical potential, the use of which supports and/or maintains the coupling of the molecule to the electrode. When thiols are adsorbed on electrodes, the adsorption potential at a pH values from 4.0 to 8.0 is in a range from 0 mV to +600 mV with respect to the Ag/AgCl electrode in 100 mM KCl, preferably the adsorption potential is approximately +300 mV. If the pH value is alkaline, the range of the adsorption potential shifts.

As defined here, the desorption potential is a potential outside the stability range defined above. The desorption potential must be sufficiently high to prevent the adsorption of molecules that are used during the immobilization process. Within a range of pH values from 4.0 to 8.0, the desorption potential is in a range beginning at −300 mV or lower with respect to the Ag/AgCl electrode in 100 mM KCl, preferably in a range from −600 mV to −1800 mV and especially in a range from −800 mV to −1400 mV.

Electrolyte solutions to be used include all aqueous solutions and organic electrolytes and mixtures thereof as well as a mixture of aqueous electrolytes and organic solvents or organic electrolytes and organic solvents.

BRIEF DESCRIPTION OF THE DRAWINGS

The figures described below present the device according to this invention as well as data measured by means of the procedure according to this invention.

DETAILED DESCRIPTION OF PREFERRED EMBODIMENTS

The device shown in FIG. 1 comprises an exchangeable device (1) for sample holders and a pump (2) which transports the desired molecules or receptors into the flow-type cell (3). In the flow-type cell (3) which contains an electrolyte solution, n electrodes are located on a support material (5). Against a reference electrode (10), either an adsorption potential (8) or a desorption potential (9) is separately applied to these electrodes by means of a multiplexer (6), which is controlled by an address bus (7). Following immobilization, the excess molecules are pumped via the pump (2) into a collecting vessel (4).

FIG. 2 is a detailed representation of the individual steps required to carry out the electrically addressable immobilization of x molecules on n electrodes. In this figure, (11) refers to the addition of a thiol-containing molecule, (12) to the adsorption of this molecule, and (13) to the rinsing with the electrolyte solution. Via pump (2), molecule A is transported into cell (3). There, molecule A is adsorbed onto electrode E1 to which the adsorption potential is applied. At the same time, the chemical adsorption on electrodes E2 to En is prevented by the desorption potential that is applied to these electrodes. The adsorption is observed and monitored by measuring the capacitance. Once the capacitance for E1 has taken on a constant value, the adsorption of molecule A is concluded, and the cell can be rinsed with the electrolyte solution. After rinsing off molecule A, the electrode potentials are changed so that the adsorption potential is maintained on E1 and the desorption potential on electrodes E3 to En. On electrode E2, the electrical potential is changed by applying the adsorption potential. Via pump (2), molecule B is transported from the exchangeable device (1) for holding the sample into the cell. There, molecule B is adsorbed only on E2 since E1 is already coated with molecule A, and the desorption potential is applied to electrodes E3 to En. The rinsing cycle is the same as the one described above. Electrodes E3 to En are coated with molecules C to X in the same way as described for electrodes E1 and E2.

Figure 3:
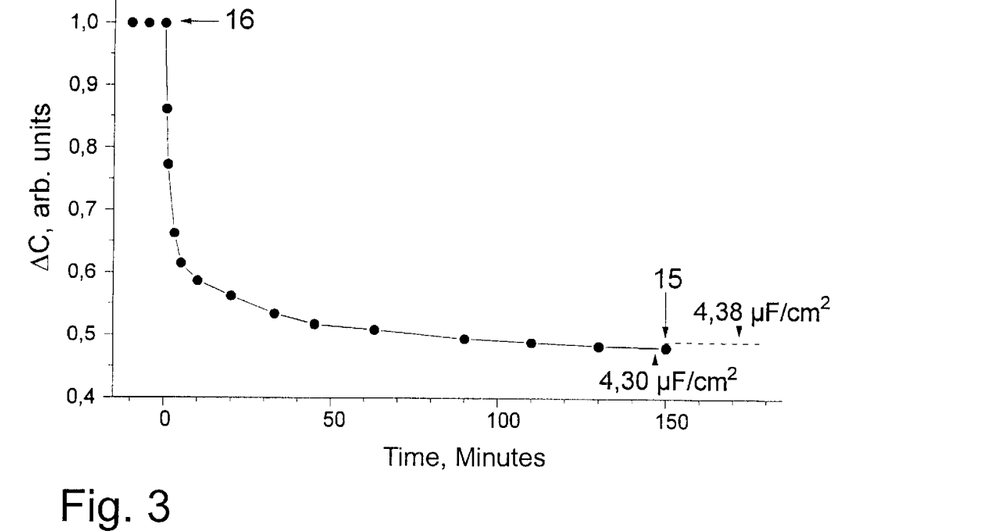
FIG. 3 presents the reduction of the capacitance (as a function of the time) of an uncoated gold electrode during the adsorption of 6-mercaptohexanoic acid at an electrode potential of +300 mV with respect to an Ag/AgCl electrode in 100 mM KCl. As a result of the fact that an electrolyte solution is subsequently used for rinsing, only a small portion of the adsorbed thiol is removed.
Figure 4:
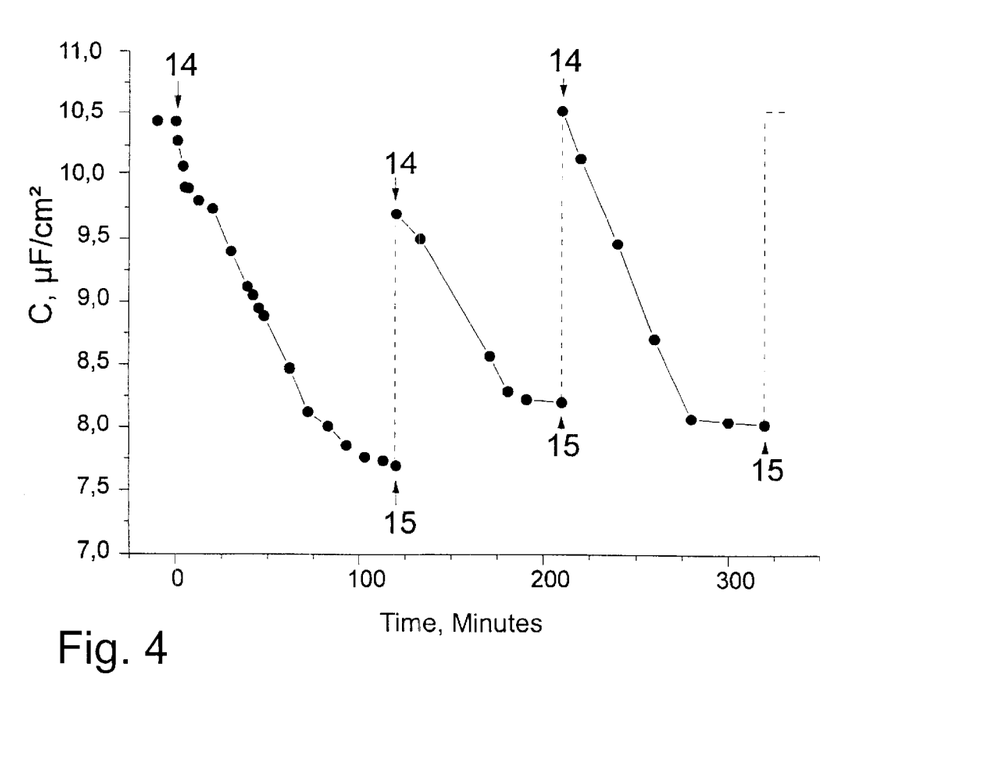
FIG. 4 presents the changes in the capacitance of an uncoated gold electrode during several adsorption and desorption cycles of octanethiol at an electrode potential of −1400 mV with respect to an Ag/AgCl electrode in 100 mM KCl. A final rinsing cycle completely removes the adsorbed thiol.
Figure 5:
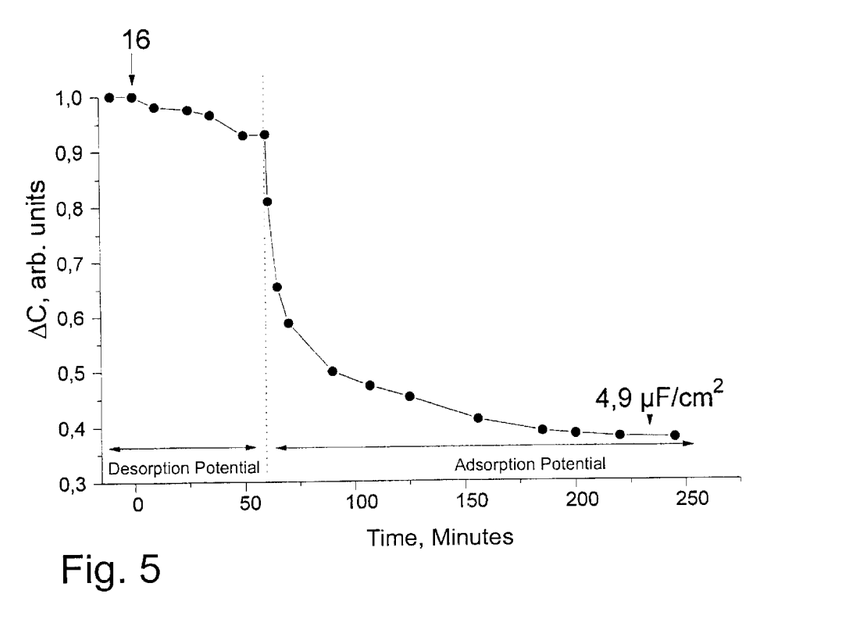
FIG. 5 presents the changes in the capacitance of an uncoated gold electrode to which, one after the other, the desorption (−1400 mV) and the adsorption potential (+300 mV) was applied against an Ag/AgCl electrode in 100 mM KCl. At both potentials, the adsorption of 6-mercaptohexanoic acid was observed and monitored.

FIGS. 3 through 5 present the changes in the capacitance that are observed during the electrically addressable immobilization with single electrodes. In these figures, (14) refers to the addition of octanethiol, (16) to the addition of 6-mercaptohexanoic acid, and (15) to the rinsing and washing of the electrodes with high-purity water and chloroform. The electrolyte used was an aqueous phosphate-buffered KCl solution (100 mM) with a pH value of 6.7. In addition, the figures also show the specific capacitance values. During the rinsing cycle, the complete removal of the thiols that were adsorbed at −1400 mV shows that these molecules had been physically adsorbed only on the gold electrode (FIG. 4). In contrast, the largest portion of the thiols that had been adsorbed at +300 mV had been chemically adsorbed and was therefore resistant to the rinsing cycle.

Figure 6:
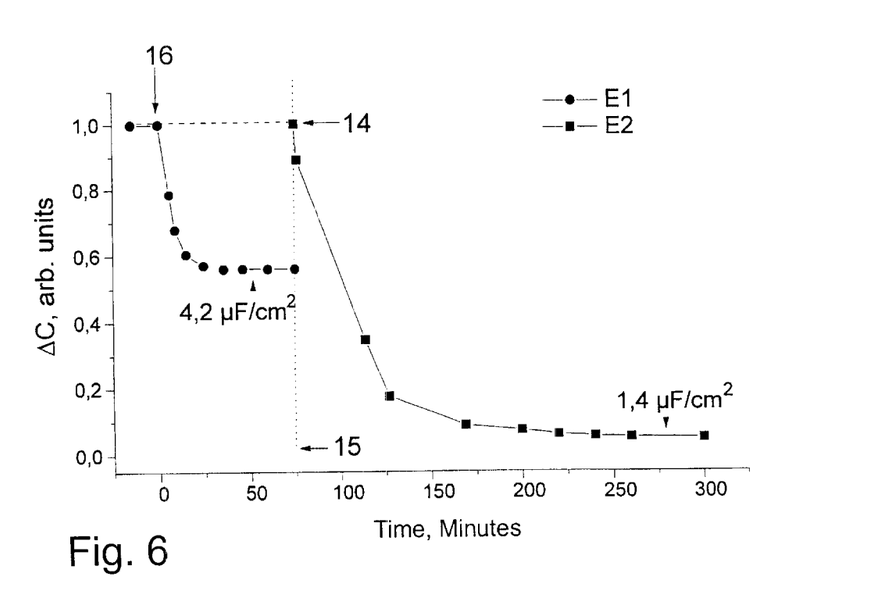
FIG. 6 presents the changes in the capacitance of a structure that comprises two gold electrodes on which the electrically addressable immobilization of 6-mercaptohexanoic acid and octanethiol was carried out at electrode potentials of +300 mV and −1400 mV, respectively, against an Ag/AgCl electrode in 100 mM KCl.

Similarly, FIG. 6 shows the result obtained with a system comprising two electrodes. The electrolyte used was an aqueous phosphate-buffered KCl solution (100 mM) with a pH value of 6.7. The addition of 6-mercaptohexanoic acid (16) and the rinsing cycle (15) took place at electrode potentials of +300 mV (adsorption potential) for electrode E1 and −1400 mV (desorption potential) for electrode E2. The addition of octanethiol (14) was carried out at an electrode potential of +300 mV for both electrodes.

The electrically addressable immobilization makes it possible to construct a multisensor system which can be used, for example, in the clinical diagnosis or in the chemical and biological analysis, e.g., for high-throughput screening. By means of the targeted construction of single electrodes, it is possible to construct a user-specific array.

With this multisensor system, it is possible, among other things, to assay enzyme activities in electrolyte solutions or biological fluids, e.g., in blood, urine, etc. For example, it is possible to determine the activity of the phospholipase $A_2$ by coupling a liposome layer by means of hydrophobic-hydrophobic interactions to an unmodified alkanethiol monolayer, e.g., hexadecanethiol or octanethiol. If phospholipase $A_2$ is present in the cell, the lipids are degraded. This can be verified on the basis of an increase in the capacitance signal.

Another multisensor system may comprise a combination of different affinity sensors. To detect an excess of human serum albumin (HSA) in the urine, which is a sign of microalbuminuria, sensors with the following structure can be used.

Figure 7:
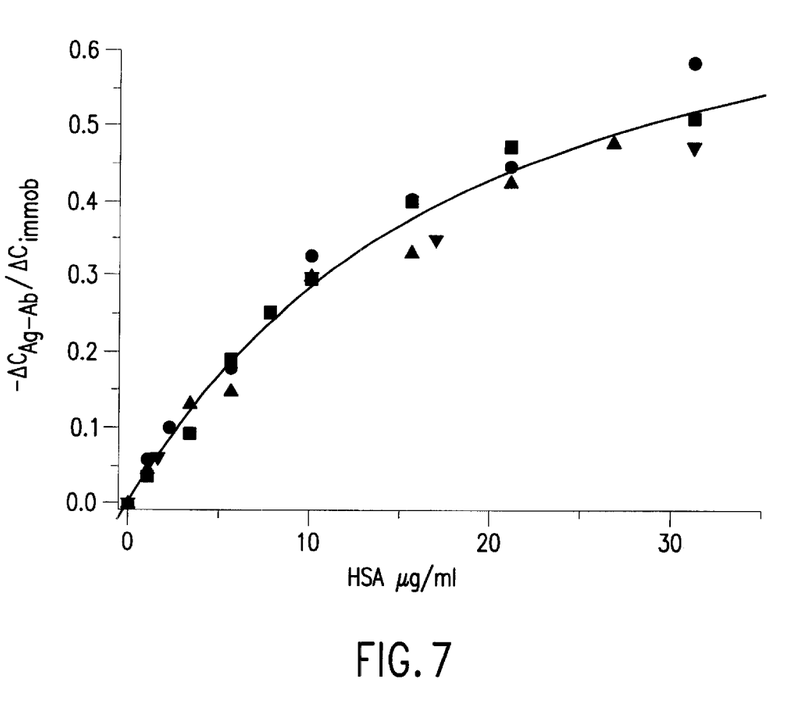
FIG. 7 presents the changes in the capacitance of HSA immunosensors during the addition of the antigen; each type of symbol indicates a sensor.

After first addressing a ω-functionalized alkanethiol, e.g., 16-mercaptohexadecanoic aid, 11-mercaptoundecanoic acid, 6-mercaptohexanoic acid, 16-mercaptohexadecaneamine, to the surface of the electrode, the covalent coupling of monoclonal anti-HSA on this monolayer takes place. This sensor structure makes it possible to detect HSA in the clinically relevant range from 1 to 30 μg/mL fluid, e.g., urine or buffer solution. The results are summarized in FIG. 7.

Other examples for using the structure according to this invention include its use as sensors for bacteriophages, as sensors for antigen-antibody assays, as DNA probes, and as immobilized LDL receptors.

Summarizing, it can be stated that the results that were obtained using the sensors according to this invention and that are shown in FIGS. 3 through 7 show that the targeted adsorption and/or desorption and/or immobilization of different molecules on specific electrodes by means of electrically addressable immobilization has been successfully accomplished. In addition, it was possible to show that the electrodes can be used as multisensors in a system. Furthermore, this invention makes available an assay system that makes it possible to successfully detect substances both quantitatively and qualitatively.

The following examples describe the procedural approach and the conditions for manufacturing the structures according to this invention with electrically addressable immobilized molecules on an electrode.

EXAMPLES

Coating Single Electrodes
Preparation of the Electrodes

Using a conventionally employed sputtering process, silicon wafer pieces having an area of 3.20 mm×10.02 mm and a thickness of 450 μm were attached to a gold electrode measuring 1.56 mm×1.56 mm (reactive surface) and a lead with a width of 10 μm and a length of 6.65 mm. The electrode was constructed from a titanium and palladium layer (coupling agents, each 50 nm thick) and a layer of gold (200 nm) as a cover. As a contact point for the measuring system, a silver-plated wire was soldered on at the upper end of the leads. Prior to cleaning, the wafer platelets were optically examined for damage by means of a reflected light microscope. Cleaning was carried out in several steps. First, the wafers were completely immersed in chloroform for 30 min. After drying in nitrogen, the wafers were immersed in a 1:1 (v/v) mixture of chloroform and methanol and treated for 10 min in an ultrasound bath. Instead of the chloroform used, it is also possible to use ethanol (99%) and a mixture of ethanol and methanol for these cleaning steps. The wafers were dried and immersed for 5 min in a hot 3:1 (v/v) mixture of concentrated sulfuric acid and 30% hydrogen peroxide solution. During the last two steps, care was taken to ensure that only the reactive electrode surface and a maximum of 4.50 mm of the lead were immersed in the mixture. The electrodes were thoroughly rinsed with high-purity water (Millipore: Milli-Q$_{Plus}$≡; 18.2 MΩcm$^{-1}$) and dried. Prior to their use, all glass and Teflon apparatuses were thoroughly cleaned as described above.

Carrying out the Measurements

The wafer plate, onto which the gold electrode had been sputtered, together with an Ag/AgCl reference electrode (with a surface of approximately 1 cm$^2$), was attached to a Teflon holder which served as the cover for the measuring cell (cap jar glass, 40 mm×19 mm) and which had an opening for adding and withdrawing fluids. The cell was filled with an electrolyte solution (100 mM KCl; pH 6.7; approximately 3 ML) to a level that ensured that the reactive surface of the gold electrode and the reference electrode (Ag/AgCl) were completely immersed. A magnetic stirrer was used to ensure that a homogeneous mixture was obtained. A lock-in amplifier with an integrated sinus generator generated a constant sinus signal with a frequency of 20 Hz and an amplitude of 10 mV. All measurements were carried out at room temperature (22° C.). The lock-in amplifier was also used to register the capacitive current. In addition to the alternating voltage, direct voltage was applied by way of a voltage sensor. As soon as molecules were adsorbed on the surface of the electrode, a change in the capacitance was measured. The measured signal was recorded on an x-t recorder and sent to the computer via a 16 bit analog-to digital converter. At the beginning of the measurement, the absolute capacitance of the uncoated gold electrode was determined at an electrical potential of +300 mV. Values of a minimum of 12–14 μF/cm$^2$ were obtained.

Adsorption Potential

After the electrode had reached a stable capacitance value, the adsorption potential (+300 mV) was maintained and enough 6-mercaptohexanoic acid, dissolved in the electrolyte solution, was added to ensure that a concentration of 50 μmol/L was present in the measuring cell. The adsorption set in immediately and was concluded after approximately 2.5 h (see FIG. 3). The half-life of the coating measured approximately 10 min, and the absolute capacitance value at 4.3 μF/cm$^2$ was comparable to that of a gold electrode that has been coated in chloroform or ethanol (1 mM 6-mercaptohexanoic acid). After the coating step was concluded, the measuring cell was opened, the gold electrodes were rinsed with high-purity water and immersed in chloroform for approximately 5 sec to remove physically adsorbed thiol from the electrodes. The reference electrode, the measuring cell, and the stirrer were thoroughly cleaned with high-purity water, chloroform, ethanol, and acetone to remove 6-mercaptohexanoic acid. Subsequently, the quality of the coating was checked by repeating the measurement of the capacitance. Compared to the values obtained earlier, only an insignificant increase in the capacitance (1–2%) was obtained.

Desorption Potential

A desorption potential of –1400 mV was applied to the gold electrode, and subsequently, time was spent waiting for the capacitance value to stabilize. Thereafter, enough octanethiol was added to ensure that a concentration of 250 μmol/L was present in the cell. The subsequent drop of the capacitance after 2 h was approximately 30% at a half-life of 45 min (see FIG. 4). At 7.8 μF/cm$^2$, the absolute capacitance value was markedly higher than that of the gold electrode which had been coated while applying the adsorption potential. After cleaning the electrode with high-purity water and chloroform (5 sec), it was found that the drop of the capacitance value was attributable only to physically adsorbed thiol since the starting values of 12–14 μF/cm$^2$ were again reached. The physical adsorption and the subsequent cleaning step were repeated several times and yielded the same result each time.

Desorption/adsorption Potential

A desorption potential of –1400 mV was applied to the gold electrode and subsequently, time was spent waiting for the capacitance value to stabilize. Next, enough 6-mercaptohexanoic acid, dissolved in electrolyte solution, was added to ensure that the concentration in the measuring cell was 50 μmol/L. The drop of the capacitance value after 1 h was approximately 7% (see FIG. 5). The applied desorption potential was subsequently replaced with the adsorption potential (+300 mV). The immediately beginning adsorption overlapped the drop of the capacitance value which was caused by the change in the potential and could therefore not be established. After approximately 2 h, the adsorption was concluded (half-life 8 min), and the absolute capacitance (4.9 μF/cm$^2$) was comparable to that of a gold electrode that had been coated in an organic solution. When the electrode was cleaned with high-purity water and ethanol (10 sec), no more adsorbed thiol was removed.

Coating a Multisensor System

Preparation of the Electrodes

Using a conventionally employed sputtering process, silicon wafer pieces having an area of 3.20 mm×10.02 mm and a thickness of 450 μm were bound to two gold electrodes measuring 1.56 mm×1.56 mm (reactive surface) and a lead with a width of 10 μm and a length of 6.65 mm. The electrode was constructed from a titanium and palladium layer (coupling agents, each 50 mn thick) and a layer of gold (200 nm) as a cover. The distance between the two electrodes was 1.56 mm. Attaching the contact point and cleaning the electrodes followed the procedure already described earlier.

Carrying out the Measurements

The wafer plate with the two gold electrodes, together with an Ag/AgCl reference electrode (with a surface of approximately 1 cm$^2$), was attached to a Teflon holder which served as the cover for the measuring cell (cap jar glass, 40 mm×19 mm) and which had an opening for adding and withdrawing fluids. The cell was filled with an electrolyte (100 mM KCl; pH 6.7; approximately 3 mL) to a level that ensured that the reactive surface of the gold electrodes and the reference electrode (Ag/AgCl) were completely immersed. A magnetic stirrer was used to ensure that a homogeneous mixture was obtained. A lock-in amplifier with an integrated sinus generator generated a constant sinus signal with a frequency of 20 Hz and an amplitude of 10 mV. All measurements were carried out at room temperature (22° C.). The lock-in amplifier was also used to register the capacitive current. In addition to the alternating voltage, direct voltage was applied by way of a voltage sensor. The two potential sensors made it possible to separately apply electric potentials (U1, U2) to the gold electrodes (E1, E2) against the Ag/AgCl reference electrode. The change in the capacitance measured was proof of the adsorption of the molecules on the surface of the electrodes. The measured signal was recorded on an x-t recorder and sent to the computer via a 16 bit analog-to digital converter. Prior to adding the first thiol, the capacitance of the uncoated gold electrode was determined at an electrode potential of U1=U2=+300 mV. Values of a minimum of 12–14 μF/cm$^2$, which are typical for uncoated gold electrodes, were obtained.

After both of the electrodes had reached stable capacitance values, the capacitance of electrode E1 was measured. The potential of +300 mV that had been applied to electrode E2 was shifted to −1400 mV. Because of this shift in the potential, time was spent waiting for the changes in the capacitance on electrode E1. Subsequently, sufficient 6-mercaptohexanoic acid, dissolved in the electrolyte solution, was added to ensure that a concentration of 50 $\mu$mol/L was present in the cell. Adsorption set in immediately and was concluded after approximately 2.5 h. The half-life of the coating was approximately 15 min, and the absolute capacity value at 4 to 5 $\mu$F/cm$^2$ was comparable to that of a gold electrode that had been coated in chloroform (1 mM 6-mercaptohexanoic acid). After the coating step was concluded, the measuring cell was opened, the gold electrodes were rinsed with high-purity water and immersed in chloroform for approximately 5 sec to remove physically adsorbed thiol from the electrodes. The reference electrode, the measuring cell, and the stirrer were thoroughly cleaned with high-purity water, chloroform, ethanol, and acetone to remove 6-mercaptohexanic acid. The measuring cell was constructed as already described above and filled with fresh electrolyte solution. At a potential of U1=U2=+300 mV, the absolute capacitance values were measured again. Electrode E1 which was coated with 6-mercaptohexanoic acid had a value of 4.2 $\mu$F/cm$^2$, the second electrode was observed during the second coating step. As octanethiol (the concentration in the cell measured 150 $\mu$mol/L) was added, adsorption set in immediately and was concluded after approximately 3 h (half-life 10.5 min). After another cleaning step, the absolute capacitance values of the two gold electrodes were 1.4 $\mu$F/cm$^2$ for electrode E2 and 4.1 $\mu$F/cm$^2$ for electrode E1.

A comparison of the prior art immobilization processes with the method according to this invention and thus with the structure obtained according to this invention shows that it is possible to make available chemo- and/or biosensors with which it is possible to carry out quantitative and qualitative assays of different types of substances and compounds. In addition, it is possible to detect the substances to be determined in a simple manner by measuring the changes in the capacitance values, preferably directly in the medium.

What is claimed is:

1. A method for producing a structure with electrically addressable immobilized molecules comprising the steps of:

providing a chamber;

providing in the chamber a non-reactive support having a plurality of electrically isolated electrodes, each having a conductive reactive surface, reactive with a compound containing one of a thiol group and a selenol group;

selecting a first at least one electrically isolated electrode of said plurality of electrically isolated electrodes for immobilizing receptor molecules on the reactive surface thereof;

introducing into the chamber an electrolyte solution containing a first set of receptor molecules comprised of a first compound containing one of a thiol group and a selenol group to be immobilized on the reactive surface of said first at least one selected electrically isolated electrode of said plurality of electrically isolated electrodes;

contacting the first at least one selected electrically isolated electrode and the reactive surface thereof with the introduced electrolyte solution;

electrically addressing the plurality of electrodes to apply an adsorption potential to said first at least one selected electrically isolated electrode while applying a desorption potential to the non-selected electrically isolated electrodes of said plurality of electrically isolated electrodes;

applying an adsorption potential to said first at least one selected electrically isolated electrode and applying a desorption potential to the non-selected electrically isolated electrodes of said plurality of electrically isolated electrodes;

chemically binding the first set of receptor molecules of the first compound in a monolayer on the reactive surface of the first at least one selected electrically isolated electrode to immobilize the first set of receptor molecules thereon; and inhibiting chemical binding of the first set of receptor molecules of the first compound on the non-selected electrodes of the plurality of electrodes and the reactive surfaces thereof thereby preventing the first set of receptor molecules of the first compound from being immobilized on the said non-selected electrodes of the plurality of electrodes.

2. A method for producing a structure with electrically addressable immobilized molecules comprising the steps of:

providing a chamber;

providing in the chamber a non-reactive support having a plurality of electrically isolated electrodes, each having a conductive reactive surface, reactive with a compound containing one of a thiol group and a selenol group;

selecting a first at least one electrically isolated electrode of said plurality of electrically isolated electrodes for immobilizing receptor molecules on the reactive surface thereof;

introducing into the chamber a first an electrolyte solution containing a first set of receptor molecules comprised of a first compound containing one of a thiol group and a selenol group to be immobilized on the reactive surface of said first at least one selected electrically isolated electrode of said plurality of electrically isolated electrodes;

contacting the first at least one selected electrically isolated electrode and the reactive surface thereof with the introduced first electrolyte solution;

electrically addressing the plurality of electrodes to apply an adsorption potential to said first at least one selected electrically isolated electrode while applying a desorption potential to the non-selected electrically isolated electrodes of said plurality of electrically isolated electrodes;

applying an adsorption potential to said first at least one selected electrically isolated electrode and applying a desorption potential to the non-selected electrically isolated electrodes of said plurality of electrically isolated electrodes;

chemically binding the first set of receptor molecules of the first compound in a monolayer on the reactive surface of the first at least one selected electrically isolated electrode to immobilize the first set of receptor molecules thereon; and inhibiting chemical binding of the first set of receptor molecules of the first compound on the non-selected electrodes of the plurality of electrodes and the reactive surfaces thereby preventing the first set of receptor molecules of the first compound from being immobilized on the said non-selected electrodes of the plurality of electrodes;

removing the first electrolyte solution from the chamber;

selecting a second at least one electrically isolated electrode of said plurality of electrically isolated electrodes from among the previously non-selected said plurality of electrically isolated electrodes for immobilizing receptor molecules on the reactive surface thereof;

introducing into the chamber a second an electrolyte solution containing a second set of receptor molecules comprised of a second compound, different from the first compound, containing a different one of a thiol group and a selenol group to be immobilized on the reactive surface of said second at least one selected electrically isolated electrode of said plurality of electrically isolated electrodes;

contacting the second at least one selected electrically isolated electrode and the reactive surface thereof with the introduced second electrolyte solution;

electrically addressing the plurality of electrodes to apply an adsorption potential to said second at least one selected electrically isolated electrode while applying a desorption potential to the remaining previously non-selected electrically isolated electrodes of said plurality of electrically isolated electrodes;

applying an adsorption potential to said second at least one selected electrically isolated electrode and applying a desorption potential to the remaining previously nonselected electrically isolated electrodes of said plurality of electrically isolated electrodes;

chemically binding the second set of receptor molecules of the second compound in a monolayer on the reactive surface of the second at least one selected electrically isolated electrode to immobilize the second set of receptor molecules thereon; and inhibiting chemical binding of the second set of receptor molecules of the second compound on the remaining previously non-selected electrodes of the plurality of electrodes and the reactive surfaces thereof thereby preventing the second set of receptor molecules of the second compound from being immobilized on the said remaining previously non-selected electrodes of the plurality of electrodes.

3. The method of claim 2 further comprising the step of coupling at least one molecular layer of a substance to at least one of the immobilized receptor molecules.

4. The method of claim 3 wherein the molecular layers are chemically or physically adsorbed to the at least one immobilized receptor molecules.

5. The method of claim 3 wherein the bonding coupling step comprises:

maintaining the adsorption potential of the selected electrodes; and introducing into the chamber a coupling reagent and an electrolyte solution containing the substance to be coupled.

6. The method of claim 5 wherein the coupling reagent is selected from the group consisting of carbodiimides and derivatives thereof and N-succinimides and derivatives thereof.

7. The method of claim 4 wherein the substance to be coupled has at least one functional group or enters into interactions with the receptor molecules and is selected from the group consisting of toxins, hormones, hormone receptors, peptides, proteins, enzymes, enzyme structures, cofactors, drugs, lectins, sugars, oligonucleotides, DNA, RNA, viruses, bacteriophages, prions, oligosaccharides, natural and artificial receptors, redox-active substances, dyes, acids, bases, epitopes, antigens, and antibodies.

8. The method of claim 1 wherein a pH value of the electrolyte solution is from 4.0 to 8.0, the adsorption potential is from 0 to +600 mV with respect to an Ag/AgCl electrode in 100 mM KCl and the desorption potential is at least −300 mV with respect to an Ag/AgCl electrode in 100 mM KCl.

9. The method of claim 1 wherein the support is a solid dielectric substrate selected from the group consisting of silicon, glass, and TEFLON, polyethylene, and polyvinyl chloride.

10. The method of claim 1 wherein the electrodes are comprised of a thin layer composed of a conductive or semiconductive material selected from the group that consists of Au, Pd, Pt, Ag, GaAs, Au/Pd, Au/Ag, and Ag/Pd.

11. The method of claim 1 wherein the receptor molecules are selected from the group consisting of molecules with formula HS—$(CH_2)_n$—X, X—$(CH_2)_n$—S—S—$(CH_2)_m$—Y, or X—$(CH_2)_n$—S—$(CH_2)_m$—Y, where m and n stand for a number from 2 to 24 and X and Y stand for H, OH, SH, $CH_3$, COOH, or $NH_2$, ω-mercapto acids, octanethiol and other n-alkanethiols, toxins, hormones, hormone receptors, peptides, proteins, enzymes, enzyme substrates, cofactors, drugs, lectins, sugars, oligonucleotides, DNA, RNA, viruses, bacteriophages, prions, oligosaccharides, natural and artificial receptors, redox-active substances, dyes, acids, bases, epitopes, and antigens or antibodies which have a minimum of one thiol group or one sulfide or disulfide group or which are coupled to a minimum of one thiol-containing compound.

12. The method of claim 1 wherein the receptor molecules have a minimum of one selenol group.

13. The method of claim 1 further comprising the step of monitoring a parameter of said selected electrode during immobilization of receptor molecules on said selected electrode.

14. The method of claim 2 wherein the support is a solid dielectric substrate selected from the group consisting of silicon, glass, TEFLON, polyethylene, and polyvinyl chloride.

15. The method of claim 2 wherein the electrodes comprised of a thin layer composed of a conductive or semiconductive material selected from the group that consists of Au, Pd, Pt, Ag, GaAs, Au/Pd, Au/Ag and Ag/Pd.

16. The method of claim 2 wherein the receptor molecules are selected from the group consisting of molecules with formula HS—$(CH_2)_n$—X, X—$(CH_2)_n$—S—S—$(CH_2)_m$—Y, or X—$(CH_2)_n$—S—$(CH_2)_m$—Y, where m and n stand for a number from 2 to 24 and X and Y stand for H, OH, SH, $CH_3$, COOH, or $NH_2$, ω-mercapto acids, octanethiol and other n-alkanethiols, toxins, hormones, hormone receptors, peptides, proteins, enzymes, enzyme substrates, cofactors, drugs, lectins, sugars, oligonucleotides, DNA, RNA, viruses, bacteriophages, prions, oligosaccharides, natural and artificial receptors, redox-active substances, dyes, acids, bases, epitopes, and antigens or antibodies which have a minimum of one thiol group or one sulfide or disulfide groups or which are coupled to a minimum of one thiol-containing compound.

17. The method of claim 2 wherein the receptor molecules have a minimum of one selenol group.

18. The method of claim 2 further comprising the step of monitoring a parameter of said selected electrode during immobilization of receptor molecules on said selected electrode.

* * * * *